United States Patent [19]

Lawrence et al.

[11] Patent Number: 5,093,117
[45] Date of Patent: Mar. 3, 1992

[54] COMPOSITIONS AND METHOD FOR THE TREATMENT OR PROPHYLAXIS OF SEPSIS OR SEPTIC SHOCK

[75] Inventors: Joyce E. Lawrence; Michael J. Griffith, both of Claremont; Melaine Alpern, Long Beach, all of Calif.

[73] Assignee: Baxter International Inc., Deerfield, Ill.

[21] Appl. No.: 300,836

[22] Filed: Jan. 24, 1989

[51] Int. Cl.$^5$ .................. A61K 37/04; A61K 37/00
[52] U.S. Cl. .................................. 424/85.8; 530/380; 514/921
[58] Field of Search .................. 424/85.8; 530/380; 514/921

[56] References Cited

U.S. PATENT DOCUMENTS 4,587,121  5/1986  Collins et al. .................. 424/85.8

FOREIGN PATENT DOCUMENTS 8501659  4/1985  PCT Int'l Appl. .................. 424/85.8

OTHER PUBLICATIONS

Taylor et al., J. Clin. Invest. vol. 79 Mar. 1987 pp. 918–925.
Young et al., Abs. *Clin. Res.* vol. 30 No. 2, 1982 p. 522A.

*Primary Examiner*—Howard E. Schain
*Assistant Examiner*—Choon P. Koh
*Attorney, Agent, or Firm*—Rothwell, Figg, Ernst & Kurz

[57] ABSTRACT

Pharmaceutical compositions useful for the treatment or prophylaxis of Gram-negative bacteremia or septic shock contain a bactericidal effective amount of polyclonal immunoglobulins against Gram-negative bacteria and a blood clot-dissolving effective amount of protein C. The compositions may further contain one or more protein C cofactors and monoclonal antibodies against Gram-negative bacterial endotoxins.

A method for the treatment or prophylaxis of Gram-negative bacteremia or septic shock comprises administering, either together or separately, a bactericidal effective amount of polyclonal immunoglobulins against Gram-negative bacteria and a blood clot-dissolving effective amount of protein C. The method may optionally include administering one or more protein C cofactors and monoclonal antibodies against Gram-negative bacterial endotoxins.

39 Claims, 1 Drawing Sheet

SCHEMATIC REPRESENTATION OF THE BIOLOGIC
EFFECTS OF GRAM-NEGATIVE ENDOTOXINS

COMPOSITIONS AND METHOD FOR THE TREATMENT OR PROPHYLAXIS OF SEPSIS OR SEPTIC SHOCK

BACKGROUND OF THE INVENTION

The present invention relates to compositions and methods for the treatment or prophylaxis of sepsis or septic shock. In a particular aspect, the invention relates to compositions and methods which, in addition to treating the underlying bacterial infection, also alleviate disturbances in the hemostatic system that contribute to septic shock.

Sepsis occurs primarily in hospitalized patients who usually have underlying diseases that render them susceptible to bloodstream invasion. In most cases of sepsis, the predominant pathogen is *Escherichia coli*, followed by the Klebsiella-Enterobacter-Serratia group and then Pseudomonas. The genitourinary tract is the most common site of infection, the gastrointestinal tract and respiratory tract being the next most frequent sources of sepsis. Other common foci are wound, burn, and pelvic infections and infected intravenous catheters.

Gram-negative bacteria have become the leading cause of fatal bacterial infections in hospital patients. The mortality rate for patients suffering from Gram-negative bacteremia has approached forty percent in the past twenty years, despite the use of antibiotics and aggressive support techniques. These bacteria are distinguished by a membrane that is relatively impermeable to drugs and by an endotoxin produced by all Gram-negative bacteria which remains lethally toxic, even after the bacterial cells have been killed. The lethality of Gram-negative infections thus is due both to uncontrolled growth of the viable bacteria and to the release of endotoxin.

Endotoxins, which are of great structural diversity and unique to Gram-negative bacteria, are associated with the lipopolysaccharide ("LPS") component of the outer membrane of the bacterial cells. The LPS from different bacterial species are structurally similar.

A serious consequence of Gram-negative bacteremia often is septic shock. Septic shock is characterized by inadequate tissue perfusion, leading to insufficient oxygen supply to tissues, hypotension and oliguria. Septic shock occurs because bacterial products, principally LPS, react with cell membranes and components of the coagulation, complement, fibrinolytic and bradykinin systems to activate coagulation, injure cells and alter blood flow, especially in the capillaries. The various effects of microbial infection on the hemostatic system are illustrated schematically in FIG. 1 of the drawings. Microorganisms frequently activate the classic complement pathway, and endotoxin activates the alternate pathway. Complement activation, leukotriene generation and the direct effects of endotoxin on neutrophils lead to accumulation of these inflammatory cells in the lungs, release of their enzymes and production of toxic oxygen radicals which damage the pulmonary endothelium and initiate the acute respiratory distress syndrome ("ARDS"). ARDS is a major cause of death in patients with septic shock and is characterized by pulmonary congestion, granulocyte aggregation, haemorrhage and capillary thrombi.

Activation of the coagulation system results in thrombin generation and platelet thrombi formation in the microcirculation in many tissues. The pathogenesis of this syndrome involves the activation of the intrinsic coagulation system by factor XII. Activated factor XII initiates the intrinsic coagulation cascade and eventually fibrinogen is converted to fibrin and clotting occurs. Uncontrolled activation of coagulation, usually accompanied by shock, will result in thrombosis and consumption of clotting factors II, V, and VIII. Some common complications of disseminated intravascular coagulation are severe clinical bleeding, thrombosis, tissue ischaemia and necrosis, haemolysis and organ failure.

At the same time, as coagulation is apparently initiated by endotoxin, countervening mechanisms also appear to be activated by clotting, namely activation of the fibrinolytic system. Activated factor XII converts plasminogen pro-activator to plasminogen activator which subsequently converts plasminogen to plasmin thereby mediating clot lysis. The activation of plasma fibrinolytic systems may therefore also contribute to bleeding tendencies.

Endotoxemia is associated with an increase in the circulating levels of tissue plasminogen activator inhibitor ("PAI"). This inhibitor rapidly inactivates tissue plasminogen activator ("tPA"), thereby hindering its ability to promote fibrinolysis through activation of plasminogen to plasmin. Impairment of fibrinolysis may cause fibrin deposition in blood vessels, thus contributing to the disseminated intravascular coagulation associated with septic shock.

Disseminated intravascular coagulation is not a complication exclusive to gram-negative infections. It has also been observed in gram-positive, fungal, and viral infections.

In view of the limited effectiveness of antibiotics in treating Gram-negative bacteremia, efforts have been made to use antibody preparations to combat Gram-negative bacterial infections. Studies have shown that intravenous preparations of polyclonal immunoglobulins can be effective in decreasing the incidence of opportunistic nosocomial Gram-negative bacterial infections, especially in immunocompromised patients. Although the polyclonal immunoglobulin is effective in killing the bacterial organisms, such preparations have proved to be generally unsatisfactory in treating septic shock.

Copending U.S. patent application Ser. No. 257,445, filed Oct. 12, 1988 and assigned to the same assignee as the present application, discloses compositions for use in the prophylaxis or treatment of Gram-negative bacteremia or endotoxic shock. These compositions comprise a combination of human polyclonal immunoglobulins containing antibodies against antigens of Gram-negative bacteria and monoclonal antibodies which are specific for epitopes common to the lipid A moiety of the lipopolysaccharides of a variety of Gram-negative bacteria. The disclosure of that application is incorporated herein by reference. The compositions described in the copending application have been found very useful for treating the underlying bacterial infection and for preventing or lessening the severity of septic shock.

It has been suggested that the plasma protein, known as protein C, plays a natural role in the defense against Gram-negative bacterial infections. See Taylor et al., *J. Clin. Invest.*, 79, 918–925 (1987). The authors of this article demonstrated that, in animals infused with live cultures of *E. coli*, high doses of activated protein C could function as an effective in vivo anticoagulant and could protect the animals against the lethal effects of the bacteria. Although protection against Gram-negative bacteria was demonstrated by Taylor et al., very high doses of protein C were required. Moreover, protein C does not affect the underlying bacterial infection, but only the hemostatic disturbances associated with the infection. In a recent presentation at the 61st Annual Meeting of the American Heart Association on Nov. 15, 1988, Taylor suggested that the dosage of protein C for treating bacteria-related coagulation disorders might be reduced by using it in combination with protein S and a monoclonal antibody to tissue factor. The feasibility of such an approach has not yet been established.

Accordingly, a need exists for compositions and methods for the treatment or prophylaxis of Gram-negative bacteremia and septic shock, which are effective against both the underlying infection and the widespread intravascular clotting which accompanies the disease.

SUMMARY OF THE INVENTION

In accordance with this invention, a composition for the treatment or prophylaxis of Gram-negative bacteremia and septic shock comprises, in a single dosage form, a bactericidal effective amount of human polyclonal immunoglobulins containing antibodies against antigens of Gram-negative bacteria and a blood clot-dissolving effective amount of activated protein C. In a particular embodiment, the composition further comprises monoclonal antibodies which are specific for epitopes common to the lipid A moiety of the lipopolysaccharides of a variety of Gram-negative bacteria.

The invention further resides in a method for the treatment or prophylaxis of Gram-negative bacteremia or septic shock, which comprises administering to a patient infected with Gram-negative bacteria a bactericidal effective amount of human polyclonal immunoglobulins containing antibodies against antigens of Gram-negative bacteria and a blood clot-dissolving effective amount of activated protein C. In a particular embodiment, the method further comprises administering to such patient monoclonal antibodies which are specific for epitopes common to the lipid A moiety of the lipopolysaccharides of a variety of Gram-negative bacteria.

Often, sepsis and actual or impending septic shock are presented to the physician as emergency situations. In such situations, the patient's well-being and, sometimes, survival depend upon immediate treatment. Accordingly, in yet another embodiment, this invention resides in a therapeutic kit for use by a physician, for example in emergency situations. Such a therapeutic kit comprises a package which contains separate containers of a polyclonal immunoglobulins and activated protein C in a form and dosage suitable for parenteral administration for the treatment of sepsis or septic shock. In a preferred embodiment, the containers are vials which contain sterile, lyophilized formulations of polyclonal immunoglobulins suitable for reconstitution.

DETAILED DESCRIPTION OF THE INVENTION

Figure 1:
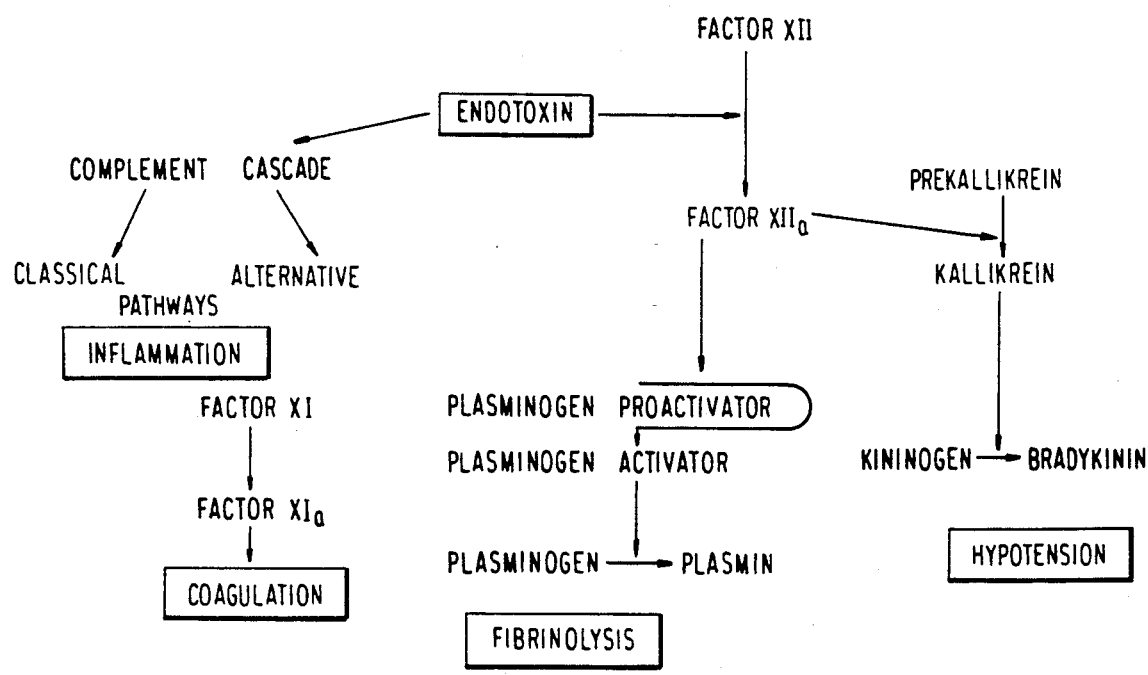
FIG. 1 is a schematic representation of the cascade of enzymatic reactions initiated by invasion of Gram-negative bacteremia, and which result in the dissemination of intravascular coagulation associated with septic shock.

The compositions and method of this invention employ activated protein C. Protein C, a vitamin K-dependent protein of blood plasma, is a protein of major physiological importance. In concert with other proteins, protein C functions both as an anticoagulant and as a fibrinolytic agent.

The mechanism of action of the activated form of protein C and the mechanism of activation of the inactive zymogen have been clarified in recent years. For a review, see J. E. Gardiner and J. H. Griffin, *Progress in Hematology*, Vol. XIII, pp. 265-278, ed. Elmer B. Brown, Grune and Stratton, Inc., 1983.

Activated protein C functions as a potent anticoagulant by selectively hydrolyzing the activated clotting cofactors, factor Va and factor VIIIa. Activated protein C only minimally degrades the inactive precursors of these clotting factors.

Activated protein C is believed to function as a fibrinolytic agent by neutralizing the fast-acting tissue plasminogen activator inhibitor ("PAI-1"). In endotoxemia, there are reportedly increased levels of PAI-1. Thus, exogenously administered protein C increases circulating levels of plasminogen activator, thereby increasing the rate of fibrinolysis.

The compositions and methods of this invention may further employ protein C cofactors in amounts sufficient to augment the activity of the protein C. An important cofactor for activated protein C is protein S, another vitamin K-dependent plasma protein. Protein S substantially increases activated protein C-mediated hydrolysis of factors Va and VIIIa.

Calcium ions also are required as a cofactor for protein C. Adequate calcium ion concentration exists in the plasma, therefore, calcium salts need not be provided in the compositions of this invention. Calcium ions have been found to stabilize activated protein C, and thus are preferably included in the compositions in stabilizing amounts.

As used herein, "protein C" and "protein S" are intended to include the mature, activated forms of the proteins, as well as biologically active fragments, analogs and derivatives thereof. The zymogens of these enzymes may also be used, but are less preferred because of possible impairment of the patient's ability to activate them. Such proteins may be naturally derived or may be produced by recombinant DNA techniques. Examples of active recombinant proteins having protein C activities are described by Bang et al. in U.S. Pat. No. 4,775,624.

The compositions and method of this invention also employ a human polyclonal immunoglobulin which contains antibodies against Gram-negative bacteria. The polyclonal immunoglobulins useful in the compositions and method of this invention can comprise purified IgG, IgM, IgA or combinations of classes of the immunoglobulins. IgG immunoglobulins are preferred. Human plasma containing normal or high levels of specific polyclonal antibodies can be used. High levels of antibody can be achieved by any one of several methods. Donors can be immunized to obtain plasma containing high titers of antibodies to one or more specific antigens, such as an antigen of *P. aeruginosa*. Alternatively, it is known that plasma from a significant portion of the human population contains naturally high levels of antibodies against Gram-negative bacteria. Thus donor plasma can be screened for high titers of naturally occurring antibodies against one or more antigens of interest, and the immunoglobulins extracted from such high-titer plasma. For purposes of this invention, plasma is considered to contain a "high titer" of antibodies to Gram-negative bacteria if the titer of these antibodies is at least 5 times greater than that of normal plasma as determined by in vitro testing. Desirably, the immunoglobulin prepared from such plasma has a titer of antibodies to Gram-negative bacteria greater than 10 times the antibody level in normal plasma pool.

A polyclonal immunoglobulin concentrate can be obtained from blood plasma using procedures known in the art, including cold ethanol precipitation, dialysis, ion exchange adsorption, and concentration by ultrafiltration. Alternative procedures include, but are not limited to, precipitation procedures using polyethylene glycol, polypropylene glycol, inorganic salts (e.g., ammonium sulfate or sodium sulfate), ion-exchange adsorptions with media containing carboxymethyl, diethylaminoethyl, or quaternary aminoethyl functional groups, immunoadsorption, affinity adsorption, isoelectric precipitation, surface adsorption, or gel filtration.

Polyclonal intravenous immunoglobulins produced by incubation at an acidic pH, incubation with trace amounts of pepsin at an acidic pH, incubation with pepsin or plasmin, reduction and alkylation, sulfonation, treatment with B-propiolactone or treatment with hydroxyethyl starch also can be used as the source of the plasma-derived polyclonal immunoglobulin to which the hybridoma-derived monoclonal antibodies are added. Alternatively, polyclonal immunoglobulins also may be formulated at a low pH (e.g., 3.5-5.5) in the presence or absence of polyhydroxy compounds such as maltose or sorbitol.

The polyclonal immunoglobulin solution then can be sterilized in accordance with conventional procedures. Then the immunoglobulin can be stabilized and stored in either a liquid or freeze-dried condition. The stable polyclonal immunoglobulins generally have concentrations ranging from about 10 mg/ml to about 200 mg/ml and are suitable for intramuscular, intraperitoneal, and intravenous injection. Undesirable side reactions are avoided by eliminating IgG aggregates, contaminants with vasoactive or coagulant potential, such as PKA or thrombin, and by the significant reduction of other non-IgG proteins, such as IgA and IgE.

Polyclonal immunoglobulin preparations that may be employed in this invention are commercially available. One such preparation is sold by Hyland Laboratories division of Baxter Healthcare Corp., Duarte, California under the trademark, Gammagard ® IVIG.

The compositions and methods of this invention employ a blood clot-dissolving effective amount of protein C. Such amount may vary, depending upon the severity of the disease, the status of the patient's hemostatic and fibrinolytic systems and the extent (if any) to which exogenous protein C cofactors are used. In general, the patient will receive from about 300 to about 6000 international units ("IU") of protein C per kg of body weight per day. Preferred dosages range from about 1000 to about 3000 IU/kg/day. The protein C is administered parenterally, preferably via intravenous, intramuscular or intraperitoneal injection. The most preferred route of administration is intravenous injection.

The compositions and methods of the invention employ a bactericidal effective amount of the polyclonal immunoglobulin. Such amount varies, depending upon the severity and type of infection, the particular immunoglobulin preparation used and whether or not adjunct therapy, such as antibiotic administration, is employed. In general, from about 100 to about 500 mg of immunoglobulins per kg of body weight per day, preferably from about 200 to about 400 mg per kg of body weight per day are administered. Like the protein C, the immunoglobulins are also administered parenterally, e.g., by intravenous, intramuscular or intraperitoneal injection. The preferred route of administration is intravenous injection.

The protein C and the polyclonal immunoglobulins are administered either separately or in combination in a pharmaceutically acceptable dosage form. They are preferably dissolved or suspended in a sterile, injectable fluid, optionally containing conventional pharmaceutical excipients. Examples of suitable injectable carriers include physiologically buffered, isotonic saline, peanut oil, and the like. The compositions may be supplied to pharmacies and physicians in the form of lyophilized powders for reconstitution with, for example, sterile saline for injection. These lyophilized powders advantageously contain stablizers such as a calcium salt and human serum albumin. Suitable calcium salts include, for example, calcium chloride, desirably present in a concentration ranging from 0.1 mM to about 10 mM. Desirable concentrations of human serum albumin are generally within the range of about 0.1% to 1%, based upon the weight of the composition.

A unit dosage form of the compositions of this invention generally contains from about 150 to about 300IU ml of protein C and from about 50 to about 150 mg/ml of polyclonal immunoglobulins in a sterile, injectable pharmaceutical carrier. A preferred unit dosage form contains from about 300 to about 1500 IU/ml of protein C and from about 75 to about 100 mg/ml of polyclonal immunoglobulins in a sterile, injectable pharmaceutical carrier.

As noted above, the compositions and method of this invention may also advantageously employ a monoclonal antibody to the LPS endotoxin component, as described in copending U.S. patent application Ser. No. 257,445, filed Oct. 12, 1988. If employed, the monoclonal antibody may be administered either separately or in combination with the protein C and the polyclonal immunoglobulins. The monoclonal antibody advantageously is administered at a dosage which is effective to contribute to the bactericidal effect of the polyclonal immunoglobulins. This dosage may vary, as the effective dosage of the polyclonal immunoglobulins varies. The monoclonal antibody dosage generally ranges from about 0.1 mg to about 3 mg per kg of patient body weight per day, preferably from about 0.25 to 1 mg/kg/day.

Injectable pharmaceutical compositions generally contain from about 0.25 to about 1 mg per ml of the monoclonal antibody, preferably from about 0.5 to about 1 mg/ml.

The compositions and method of this invention also advantageously may contain an effective amount of protein S. The protein S is administered either separately or in combination with the protein C in the same manner as the protein C. Effective dosages of protein S will vary, but generally range from about 0.1 to about 10 mg per kg of patient body weight per day. Preferred dosages of protein S range from about 1 to about 5 mg/kg/day.

Also contemplated within the present invention is a therapeutic kit for use by physicians, for example, in emergency situations. Such a kit may be stocked by hospital pharmacies and emergency rooms for immediate and convenient use. In general, such a kit will comprise a package containing separate containers of polyclonal immunoglobulins and protein C in dosage forms and amounts suitable for parenteral administration, either directly or upon reconstitution. The kit will also contain instructions to the physician or health care professional for its use. Preferably, the containers are vials which contain the polyclonal immunoglobulins and the protein C in the form of sterile, lyophilized powders for reconstitution with a sterile injectable vehicle, such as normal saline. The reconstitutable, lyophilized forms of the proteins are generally more stable than solutions and thus have convenient shelf lives. The kit may also contain a separate vial of the injectable vehicle, optionally also including a sterile syringe, of appropriate size. The vials contain at least one dose of each of the components and preferably contain no more doses than will be administered within the shelf life of the product after opening or reconstitution.

Such a kit, for example, can contain 4 vials of intravenous immunoglobulin (2.5 g each vial) and 1 vial of activated protein C (100 mg). The IGIV, when reconstituted with the appropriate volume of diluent, contains approximately 1% sodium chloride, not more than 20 mg/ml glucose, not more than 0.2 g/dl PEG, and 0.3 M glycine as a stabilizing agent. Activated protein C can be formulated into an injectable preparation by mixing the sample with a suitable vehicle for injection such as a buffer (phosphates, sodium chloride, etc.), an isotonic agent, a filler (e.g. mannitol, dextran, etc.), a stabilizer (e.g. albumin) and dissolving the mixture in distilled water, then freeze-drying the solution to obtain a composition which is filled in a vial for injection. The main route of administration of the IGIV and APC is by intravenous infusion, and this can be carried out with each parenteral solution contained within an infusion bag or bottle. The solutions can be delivered simultaneously to the patient, via a Y-connection, through the use of an infusion pump. In this embodiment, the total dose of IGIV is 10 g, administered at 200 mg/kg and the dose of APC is 100 mg, administered at 2 mg/kg.

The invention is further illustrated by the following examples, which are not intended to be limiting.

EXAMPLE 1

Preparation of Therapeutic Mixtures a. Purification of Human Protein C

Protein C was purified by immunoaffinity chromatography from a commercially available Factor IX concentrate obtained from Hyland Laboratories, Duarte, California under the trademark, Proplex.

For each preparation of protein C, 10 bottles of Proplex concentrate were each suspended in 5 ml of 0.02 M tris, 0.15 M sodium chloride pH 7.4 (tris-buffered saline). The suspension was applied to a 12 ml column of anti protein C monoclonal antibody coupled to Sepharose CL-4B at an antibody concentration of between 2 mg and 5 mg per ml of resin. Following sample application at a flow rate of 30 ml/h, the column was washed with six volumes of tris-buffered saline. Protein C was subsequently eluted from the monoclonal antibody column using 3 M potassium thiocyanate in tris-buffered saline.

The protein C eluted in this way was dialyzed exhaustively against tris-buffered saline to remove the thiocyanate, and stored at $+5°$ C. in the presence of 0.02% sodium azide.

b. Activation of Protein C

Protein C was activated by either of two different methods.

(i) Thrombin Activation

Protein C prepared by immunoaffinity as described, was dialyzed against 0.05 M tris/$H_3PO_4$ pH 8.0 and then mixed with human thrombin at a ratio of 4 mg of thrombin per 100 mg of protein C. The mixture was incubated at 37° for 90 minutes and then the pH was adjusted to 6.5 using 0.1 M $H_3PO_4$. The sample was then applied to a column of S-Sepharose pre-equilibrated with 0.5 M sodium phosphate buffer pH 6.5. Activated protein C did not bind to the resin under these conditions and was collected in the flow-through. Thrombin could be eluted in the presence of 0.3 M sodium phosphate buffer pH 6.5.

c. Assay of Purified Protein C Preparations

Protein C, purified from Proplex concentrate as described, was measured in each of two ways:

(i) Chromoqenic Assay

Chromogenic assay was performed essentially as described in the literature (Martinoli, J.L., and K. Stocker, *Thromb. Res.* 43: 253 [1986]; Francis, R.B., Jr. and U. Seyfert, *Am. J. Clin. Pathol.* 87: 619 [1987]) using Protac (a specific and rapid protein C activator from the venom of Agkistrodon contortrix contortrix) as the activator of protein C. In this assay 10 μl of appropriately diluted sample was placed in individual wells of a 96-well microtiter plate. Fifty μl of Protac or normal saline was then added to each well and the plate incubated at room temperature of 15 min. At this time, 100 μl of imidazole/tris buffer pH 8.3 was added to each well and the plate incubated for a further 5 min. Fifty μl of substrate (S-2366) at a concentration of 2mM was then added to each sample and the plate was left at room temperature of 25 minutes. The final step involves stopping the reaction with 50 μl of 50% (w/v) acetic acid. The $A_{405}-A_{492}$ is then measured in a 96-well microtitre plate reader and the concentration of protein C in unknown samples determined by comparison with the absorbances of known protein C standard.

(ii) Immunoelectrophoresis

The concentration of protein C in immunopurified preparations was also measured using an immuno-electrophoretic procedure for measuring protein C antigen. This was carried out essentially as described in the published literature. See, Griffin, J.H., et al., *J. Clin. Invest.* 68: 1370 (1981).

(iii) Protein C Activator (PCA) Activation

Protein C activator was prepared as described in the literature. Orthner, C.L., et al., *Thromb. Haemastas,* 58: Abstract # 1014 (1978). Prior to activation, protein C isolated by immunoaffinity chromatography as described, was dialyzed against 0.05 M tris, 20 mM sodium chloride pH 7.5. The dialyzed pool was then mixed with protein C activator at a ratio of 1:1000, activator to protein C.

d. Preparation of Activated Protein C for Injection

All pools of activated protein C were concentrated to approximately 2 mg/ml using ultrafiltration, and dialyzed exhaustively against tris-buffered saline. Each preparation was then passed over a column polymyxin B to remove pyrogens. The average endotoxin concentration of preparations of activated protein C was >1EU/ml.

EXAMPLE 2

In Vivo Demonstration of Efficacy of Activated Protein C/Polyclonal Immunoglobulins Preparation The challenge organism used was a strain of *Escherichia coli* (2735). This is a clinical isolate from the City of Hope National Medical Centre, Duarte, California. Three groups of 10 female CFW mice each, were injected intravenously with the chosen sample containing approximately $1 \times 10^6$, $1 \times 10^7$ or $1 \times 10^8$ colony forming units of *E. coli*. These doses were chosen to facilitate calculation of $LD_{50}$ values. Each mouse weighed approximately 20 g and received a total volume of 0.33 ml.

The challenge groups received the following preparations:
1. 1% human serum albumin (HSA) in tris-buffered saline.
2. 1 μg human thrombin in 1% HSA
3. 0.4 μg protein C activator (PCA) in 1% HSA
4. 15 mg intravenous polyclonal immunoglobulin (Gammagard ® IVIG)
5. 15 mg Gammagard + 1 μg thrombin
6. 15 mg Gammagard 0.4 μg PCA
7. 200 μg thrombin-activated protein C
8. 400 μg thrombin-activated protein C
9. 200 μg thrombin-activated protein C + 15 mg Gammagard
10. 400 μg thrombin-activated protein C + 15 mg Gammagard
11. 200 μg PCA-activated protein C
12. 400 μg PCA-activated protein C
13. 200 μg PCA-activated protein C + 15 mg Gammagard
14. 400 μg PCA-activated protein C + 15 mg Gammagard After 7 days, the experiment was terminated. The data was analyzed in a number of ways. Firstly, a strengthened chi-square test was used, consisting of a combination of 2×2 contingency tables. Secondly, $LD_{50}$ studies were performed, using the Spearman-Karber method for assays of quantal response.

As shown in Table 1, protein C activated with human thrombin, improved the survival of mice challenged with live *E. coli*. In this particular experiment, the Gammagard polyclonal immunoglobulin preparation was used as a positive control, and the effect of activated protein C, when combined with polyclonal immunoglobulins, was not investigated.

In separate experiments, when activated protein C was combined with intravenous immune globulin, the number of survivors receiving the preparation was greater than the number of mice which survived when either activated protein C or the polyclonal immunoglobulin preparation was administered alone. Furthermore, the therapeutic effect of protein C was evident whether the protein C was activated with thrombin or with the protein C activator isolated from snake venom.

These results show that the combination of activated protein C and polyclonal immunoglobulins is effective in the treatment of sepsis and/or septic shock caused by bacterial infection.

TABLE I

Effect of Activated Protein C (APC) on Mice Challenged with *E. coli* 2735

| *E. coli* 2735, # of organisms Treatment | $10^6$ | $10^7$ | $10^8$ |
|---|---|---|---|
| | Number of Survivors | | |
| 1% human serum albumin (HSA) in tris-buffered saline (TBS) | 10 | 1 | 0 |
| 15 mg intravenous immune globulin (IGIV) | 10 | 10 | 0 |
| 1 μg human thrombin ($II_a$) in HSA | 9 | 3 | 0 |
| 200 μg APC, activated with $II_a$ | 10 | 8 | 0 |
| 400 μg APC, activated with $II_a$ | 10 | 6 | 0 |

| 2 × 2 Contingency Test | |
|---|---|
| Comparison of: | p - value |
| HSA versus IGIV | 2p < .003** |
| Thrombin | 2p > .617 |
| Thrombin versus 200 μg protein C, activiated with thrombin | 2p = .014** |
| Thrombin versus 400 μg protein C, activated with thrombin | 2p = .099 |
| IGIV versus 200 μg protein C, activated with thrombin | 2p = .136 |
| IGIV versus 400 μg protein C, activated with thrombin | 2p = .025** |

**Statistically Significant

TABLE 2

Combined Effect of Activated Protein C (APC) and Intravenous Immune Globulin IGIV on Mice Challenged with *E. coli* 2735

| *E. coli* 2735, # of organisms Treatment | $10^6$ | $10^7$ | $10^8$ |
|---|---|---|---|
| | Number of Survivors | | |
| 1% HSA in TBS | 10 | 8 | 0 |
| 1 μg $II_a$ in 1% HSA | 10 | 8 | 3 |
| 15 mg IGIV | 10 | 6 | 0 |
| 1 μg $II_a$ + 15 mg IGIV | 10 | 8 | 2 |
| 200 μg $II_a$-activated PC | 10 | 8 | 2 |
| 400 μg $II_a$-activated PC | 10 | 6 | 0 |
| 200 μg $II_a$-activated PC + 15 mg IGIV | 10 | 7 | 3 |
| 400 μg $II_a$-activated PC + 15 mg IGIV | 10 | 10 | 6 |

| Treatment | $LD_{50}$ (CFU) |
|---|---|
| 1% HSA in TBS | $3.6 \times 10^7$ |
| 1 μg $II_a$ in 1% HSA | $7.2 \times 10^7$ |
| 15 mg IGIV | $2.3 \times 10^7$ |
| 1 μg $II_a$ + 15 mg IGIV | $5.7 \times 10^7$ |
| 200 μg $II_a$-activated PC | $5.7 \times 10^7$ |
| 400 μg $II_a$-activated PC | $2.3 \times 10^7$ |
| 200 μg $II_a$-activated PC + 15 mg IGIV | $5.7 \times 10^7$ |
| 400 μg $II_a$-activated PC + 15 mg IGIV | $>1.8 \times 10^8$ |

| 2 × 2 Contingency Test | |
|---|---|
| Comparison of: | p - value |
| IGIV + 400μg $II_a$-activated protein C versus HSA | 2p < .003** |
| IGIV + 400 μg $II_a$-activated protein C versus IGIV | 2p < .003** |
| IGIV + 400 μg $II_a$-activated protein C versus IGIV + 200 μg APC | 2p = .029** |
| IGIV + 400 μg $II_a$-activated protein C versus 400 μg $II_a$-activated protein C | 2p ≤ .003** |

**Statistically Significant

TABLE 3

Combined Effect of on Mice Challenged with *E. coli* 2735

| *E. coli* 2735, # of organisms Treatment | $10^6$ | $10^7$ | $10^8$ |
|---|---|---|---|
| | Number of Survivors | | |

TABLE 3-continued

| Combined Effect of on Mice Challenged with E. coli 2735 | | | |
|---|---|---|---|
| 1% HSA in TBS | 10 | 6 | 0 |
| 0.4 μg protein C activator (PCA) | 9 | 6 | 0 |
| 15 mg IGIV | 10 | 8 | 0 |
| 0.4 μg PCA + 15 mg IGIV | 10 | 8 | 0 |
| 200 μg PCA-activated protein C | 10 | 4 | 0 |
| 400 μg PCA-activated protein C | 10 | 4 | 0 |
| 200 μg PCA-activated protein C + 15 mg IGIV | 10 | 10 | 0 |
| 400 μg PCA-activated protein C + 15 mg IGIV | 10 | 10 | 3 |

| Treatment | $LD_{50}$ (CFU) |
|---|---|
| 1% HSA in TBS | $1.8 \times 10^7$ |
| 0.4 μg PCA | $1.4 \times 10^7$ |
| 15 mg IGIV | $2.8 \times 10^7$ |
| 0.4 μg PCA + 15 mg IGIV | $2.8 \times 10^7$ |
| 200 μg PCA-activated protein C | $1.1 \times 10^7$ |
| 400 μg PCA-activated protein C + 15 mg IGIV | $1.1 \times 10^7$ |
| 200 μg PCA-activated protein C + 15 mg IGIV | $4.4 \times 10^7$ |
| 400 μg $II_a$-activated PC + 15 mg IGIV | $8.8 \times 10^7$ |

| 2 × 2 Contingency Test | |
|---|---|
| Comparison of: | p - value |
| 15 mg IGIV + 400 μg PCA-activated protein C versus 15 mg IGIV | 2p = .016** |
| 15 mg IGIV + 400 μg PCA-activated protein C versus 400 μg PCA activated protein | 2p < .003** |

**Statistically Significant

We claim:

1. A composition for the treatment or prophylaxis of Gram-negative bacteremia and septic shock, which comprises, in a single dosage form, a bactericidal effective amount of human polyclonal immunoglobulins containing antibodies against antigens of Gram-negative bacteria and a blood clot-dissolving effective amount of activated protein C.

2. The composition of claim 1, wherein the polyclonal immunoglobulins have a titer of antibodies to one or more antigens of Gram-negative bacteria in a range of at least 5 times that found in normal plasma.

3. The composition of claim 1, wherein the polyclonal immunoglobulins have a titer of antibodies to one or more antigens of Gram-negative bacteria in a range of at least 10 times that found in normal plasma.

4. The composition of claim 3, wherein the polyclonal immunoglobulins are isolated from plasma obtained from human donors who have been vaccinated with a Gram-negative bacterial antigen vaccine.

5. The composition of claim 3, wherein the polyclonal immunoglobulins are isolated from plasma obtained from human donors who possess naturally high antibody titer to at least one Gram-negative organism.

6. The composition of claim 1, wherein the protein C is naturally derived, activated protein C.

7. The composition of claim 1, wherein the protein C is recombinant activated protein C.

8. The composition of claim 1, wherein the polyclonal immunoglobulins and the protein C are dissolved or suspended in a sterile injectable fluid.

9. The composition of claim 8, wherein the concentration of the polyclonal immunoglobulins is from about 50 to about 150 mg per ml., and the concentration of the protein C is from about 150 to about 3000 IU per ml.

10. The composition of claim 8, wherein the concentration of the polyclonal immunoglobulins is from about 75 to about 100 mg per ml., and the concentration of the protein C is from about 300 to about 1500 IU per ml.

11. The composition of claim 9, which further comprises protein S in an amount sufficient to augment the biological activity of the protein C.

12. The composition of claim 9, wherein the concentration of the protein S is from about 0.1 to about 10 mg per ml.

13. The composition of claim 9, wherein the concentration of the protein S is from about 1 mg to about 5 mg per ml.

14. The composition of claim 9, which further comprises a monoclonal antibody to the lipid A moiety of the lipopolysaccharides of Gram-negative bacteria in a bactericidal effective amount.

15. The composition of claim 14, wherein the concentration of the monoclonal antibody is from about 0.25 to about 1 mg per ml.

16. The composition of claim 14, wherein the concentration of the monoclonal antibody is from about 0.5 to about 1 mg per ml.

17. The composition of claim 1, which is in lyophilized form in a sealed container for reconstitution with a sterile, injectable fluid.

18. A method for the treatment or prophylaxis of Gram-negative bacteremia or septic shock, which comprises administering to a patient infected with Gram-negative bacteria a bactericidal effective amount of human polyclonal immunoglobulins containing antibodies against antigens of Gram-negative bacteria and a blood clot-dissolving effective amount of activated protein C.

19. The method of claim 18, wherein the polyclonal immunoglobulins have a titer of antibodies to one or more antigens of Gram-negative bacteria in a range of at least 5 times that found in normal plasma.

20. The method of claim 18, wherein the polyclonal immunoglobulins have a titer of antibodies to one or more antigens of Gram-negative bacteria in a range of at least 10 times that found in normal plasma.

21. The method of claim 20, wherein the polyclonal immunoglobulins are isolated from plasma obtained from human donors who have been vaccinated with a Gram-negative bacterial antigen vaccine.

22. The method of claim 20, wherein the polyclonal immunoglobulins are isolated from plasma obtained from human donors who possess naturally high antibody titer to at least one Gram-negative organism.

23. The method of claim 18, wherein the protein C is naturally derived, activated protein C.

24. The method of claim 18, wherein the protein C is recombinant activated protein C.

25. The method of claim 18, wherein the polyclonal immunoglobulins and the protein C are administered parenterally dissolved or suspended in a sterile injectable fluid.

26. The method of claim 25, wherein the polyclonal immunoglobulins and the protein C are administered separately.

27. The method of claim 25, wherein the polyclonal immunoglobulins and the protein C are administered together in the same injectable fluid.

28. The method of claim 25, wherein the polyclonal immunoglobulins are administered by intravenous injection.

29. The method of claim 25, wherein the polyclonal immunoglobulins are administered at a dosage of from about 100 to about 500 mg per kg of patient body weight per day, and the protein C is administered at a dosage of from about 300 to about 6000 IU per kg of patient body weight per day.

30. The method of claim 25, wherein the polyclonal immunoglobulins are administered at a dosage of from about 200 to about 400 mg per kg of patient body weight per day, and the protein C is administered at a dosage of from about 1000 to about 3000 IU per kg of patient body weight per day.

31. The method of claim 29, which further comprises administering protein S in an amount sufficient to augment the biological activity of the protein C.

32. The method of claim 29, wherein the protein S is administered at a dosage of from about 0.1 to about 10 mg per kg of patient body weight per day.

33. The method of claim 29, wherein the protein S is administered at a dosage of from about 1 to about 5 mg per kg of patient body weight per day.

34. The method of claim 29, which further comprises administering to said patient a monoclonal antibody to the lipid A moiety of the lipopolysaccharides of Gram-negative bacteria in a bactericidal effective amount.

35. The method of claim 34, wherein the monoclonal antibody is administered at a dosage of from about 0.1 mg to about 3 mg per kg of patient body weight per day.

36. The method of claim 34, wherein the monoclonal antibody is administered at a dosage of from about 0.25 mg to about 1 mg per kg of patient body weight per day.

37. A therapeutic kit, which comprises a package which contains separate containers of a polyclonal immunoglobulins and activated protein C in a form and dosage suitable for parenteral administration for the treatment of sepsis or septic shock.

38. The therapeutic kit of claim 37, wherein the containers are vials which contain sterile, lyophilized formulations of polyclonal immunoglobulins suitable for reconstitution.

39. The therapeutic kit of claim 38, which further comprises instructions for use of the product and a container of sterile vehicle for reconstituting the lyophilized protein C and polyclonal immunoglobulins.

* * * * *